United States Patent
Van Dyke et al.

(10) Patent No.: US 11,896,571 B2
(45) Date of Patent: *Feb. 13, 2024

(54) METHODS FOR INCREASING ORAL OSTEOGENESIS USING LIPOXIN $A_4$ ($LXA_4$) AND ITS ANALOGS

(71) Applicant: Forsyth Dental Infirmary for Children, Cambridge, MA (US)

(72) Inventors: Thomas E. Van Dyke, West Roxbury, MA (US); Hatice Hasturk, Brighton, MA (US); Alpdogan Kantarci, Brighton, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,602

(22) Filed: Oct. 7, 2019

(65) Prior Publication Data
US 2020/0138763 A1 May 7, 2020

Related U.S. Application Data

(63) Continuation of application No. 14/769,736, filed as application No. PCT/US2013/031891 on Mar. 15, 2013, now Pat. No. 10,434,080.

(60) Provisional application No. 61/767,298, filed on Feb. 21, 2013.

(51) Int. Cl.
*A61K 31/202* (2006.01)
*A61K 9/00* (2006.01)
*A61K 45/06* (2006.01)
*A61P 19/10* (2006.01)

(52) U.S. Cl.
CPC .......... *A61K 31/202* (2013.01); *A61K 9/0053* (2013.01); *A61K 9/0063* (2013.01); *A61K 45/06* (2013.01)

(58) Field of Classification Search
CPC .. A61K 31/202; A61K 9/0063; A61K 9/0053; A61K 45/06
See application file for complete search history.

(56) References Cited

U.S. PATENT DOCUMENTS

| | | | |
|---|---|---|---|
| 5,648,512 A ‡ | 7/1997 | Serhan ................. | A61K 31/557 560/103 |
| 7,700,650 B2 ‡ | 4/2010 | Van Dyke ............ | A61K 31/202 514/549 |
| 7,812,054 B2 ‡ | 10/2010 | Van Dyke ............ | A61K 31/202 514/549 |
| 10,434,080 B2 * | 10/2019 | Van Dyke ............... | A61P 29/00 |
| 2011/0009488 A1 ‡ | 1/2011 | Bazan ....................... | A01N 1/02 514/560 |
| 2011/0104265 A1 ‡ | 5/2011 | Mousa .................. | A61K 31/351 424/451 |

FOREIGN PATENT DOCUMENTS

| EP | 2958560 A1 | 12/2015 |
|---|---|---|
| WO | WO 0170664 ‡ | 9/2001 |
| WO | WO 2008057283 ‡ | 5/2008 |
| WO | WO-2008/068041 A1 | 6/2008 |

OTHER PUBLICATIONS

Pouliot et al, (Lipoxin A4 Analogues Inhibit Leukocyte Recruitment to Porphyromonas gingivalis: A Role for Cyclooxygenase-2 and Lipoxins in Periodontal Disease), Biochemistry 2000, 39, 4761-4768. (Year: 2000).*
Kantarci et al (Lipoxin signaling in neutrophils and their role in periodontal disease) Science direct, Elsevier, pp. 289-299. (Year: 2005).*
Schonfeld (Strategies for managing periodontal inflammation), Journal of the California dental association, pp. 272-283. (Year: 2010).*
Serhan, C. N., "Clues for New Therapeutics in Osteoporosis and Periodontal Disease: new roles for lipoxygenases?" Expert Opin. Ther. Targets, 8(6):643-652 (2004).‡
Supplementary European Search Report for EP 13 87 5725 prepared on Sep. 20, 2016.‡
Pouliot, M. et al., "Lipoxin A4 and aspirin-triggered 15-epi-LXA4 inhibit tumor necrosis factor-a-initiated neutrophil responses and trafficking: novel regulators of a cytokine-chemokine axis relevant to periodontal diseases," J. Periodont Res 34:370-373 (1999).‡
Borgeson, E. et al., "Lipoxin A4 Inhibits Porphyromonas gingivalis-Induced Aggregation and Reactive Oxygen Species Production by Modulating Neutrophil-Platelet Interaction and CD11 b Expression," Infection and Immunity, 79:1489-1497 (2011).‡
Romano, M., "Lipoxin and Aspirin-Triggered Lipoxins," TheScientificWorldJournal, 10:1048-1064 (2010).‡
Borchard, R. et al., "Incisions and Tissue Management in Periodontal Surgery," Perio, 1(2):111-122(2004).‡
Petasis et al; Design and synthesis of benzo-lipoxin A4 analogs with enhanced stability and potent anti-inflammatory properties; Bioorganic & Medicinal chemistry letters 18 (2008) 1382-1387.‡
Symons et al; Effect of lipoxin A4 on bone healing in the rat mandible; Australian Dental Journal ADRF special research supplement 2007; 52.4.‡

* cited by examiner
‡ imported from a related application

*Primary Examiner* — Mina Haghighatian
(74) *Attorney, Agent, or Firm* — Foley Hoag LLP; Hathaway P. Russell (57) ABSTRACT

The invention provides methods for increasing oral osteogenesis using $LXA_4$ and its analogs. Methods are also provided for treating or preventing oral disorders that would benefit from increased oral osteogenesis using $LXA_4$ and its analogs.

13 Claims, 4 Drawing Sheets

METHODS FOR INCREASING ORAL OSTEOGENESIS USING LIPOXIN A$_4$ (LXA$_4$) AND ITS ANALOGS

CROSS-REFERENCE TO RELATED APPLICATIONS

This application is a continuation of U.S. application Ser. No. 14/769,736, filed Aug. 21, 2015, now U.S. Pat. No. 10,434,080, which is a U.S. 371 National Stage Application of International Application No. PCT/US13/031891, filed Mar. 15, 2010, which claims the benefit of U.S. Provisional Application No. 61/767,298, filed on Feb. 21, 2013; the entire content of each of these applications are incorporated herein in their entirety by this reference.

BACKGROUND OF THE INVENTION

Oral health disorders, such as gum disease and periodontitis, are widespread among modern human populations. Indeed, in the U.S. it is estimated that nearly 1 out of 2 American adults—aged 30 and older—have mild to severe periodontitis (Eke et al. (2012) *J. Dent. Res.* 91:914-920). The severity of such conditions increases when they are not treated and can lead not only to local oral problems, such as bone and early tooth loss, but also systemic disorders, such as heart disease.

In particular, periodontitis is a local inflammation that occurs as a result of host response against specific microorganisms and eventually leads to the tissue destruction and systemic complications. Once periodontal inflammation is initiated, the cascade of inflammatory events includes an amplified loop until the infection is contained and injury is confined (Genco (1992) *J. Periodontol.* 63 (4 Suppl.): 338-355). The early actions of the host response are later replaced by more specific mechanisms and eventually become redundant. Thus, it is important, as in other biologic processes, to limit the response and to allow the inflammation to resolve. While it has been shown that many molecules ("on signals") participate in the initiation and development of the host defense mechanisms, a recent paradigm in periodontal disease pathogenesis emphasizes the importance of counterregulatory molecules ("off signals") in the resolution of inflammatory response to control its magnitude and duration (Van Dyke (2011) *J. Clin. Periodontol.* 38 (Suppl. 11) 119:125). Omega-3 polyunsaturated fatty acids (n-3 PUFA) are essential fatty acids provided by dietary sources and exert anti-inflammatory effects to limit the inflammatory cascade due to their hypolipidemic properties. Resolvins are derived from omega-3 fatty acids, EPA and DHA (resolvin E1 and resolvin D1 respectively). The anti-inflammatory and proresolving actions of the resolvins and protections (also derived from DHA) have already been documented in several animal models of inflammatory diseases and tissue injury including periodontal disease (Serhan et al. (2003) *J. Immunol.* 171:6856-6865; Hasturk et al. (2006) *FASEB J.* 20:401-403; Hasturk et al. (2007) *J. Immunol.* 179:7021-7029). In rabbit periodontitis and inflammation-induced bone destruction, one of the resolvins, i.e., resolvin E1 (RVE1) reduces inflammation protects from bone loss and stimulates tissue regeneration (Hasturk et al. (2006) *FASEB J.* 20:401-403; Hasturk et al. (2007) *J. Immunol.* 179:7021-7029).

Despite these results, however, few agonists of endogenous resolution programs, as opposed to inhibitors of the inflammatory process or immunosuppressives, are known. Rather than treating or preventing the root causes of oral conditions that would benefit from increased oral osteogenesis, current dental practices are largely limited to surgical procedures to treat the results. For example, current periodontal surgical procedures include open flap debridement, osseous surgery, and guided tissue regeneration and bone grafting. In cases of moderate to advanced periodontitis, surgical treatment, when coupled with regular post-treatment maintenance of the periodontal space, often results in little to no further breakdown of the site, and the halting of tooth loss in approximately 85% of patients (Kaldahl et al. (1996) *J. Periodontol.* 67:103-108). However, current procedures provide minimal tissue (e.g., bone) regeneration potential. Prevention strategies and associated therapies are generally aimed at removal of calculus and microorganisms that lead to periodontal breakdown and then maintenance of a healthy space, as opposed to rebuilding damaged and/or lost tissue. Thus, there is a great need to identify agents that can increase oral osteogenesis and methods for treating and preventing oral conditions that would benefit from increased oral osteogenesis using such agents.

SUMMARY OF THE INVENTION

The present invention is based, at least in part, on the discovery that lipoxin A$_4$ (LXA$_4$) and its analogs can increase oral osteogenesis. Thus, in one aspect of the invention, lipoxin A$_4$ (LXA$_4$) and its analogs may be used to treat or prevent oral conditions. In certain embodiments, the oral condition is one in which increased oral osteogenesis, such as periodontitis, would be beneficial to the subject. In certain embodiments, the present invention further contemplates that other oral tissues may be regenerated, such oral tissues may include soft tissues, including epithelium, and connective tissues, such as collagen and blood vessels.

In one aspect, the present invention provides a method of treating or preventing an oral disorder that would benefit from increased oral osteogenesis in a subject in need thereof comprising administering a therapeutically effective amount of LXA$_4$ or an analog thereof to the oral cavity of the subject to thereby treat or prevent the oral disorder that would benefit from increased oral osteogenesis. In one embodiment, the oral disorder is selected from the group consisting of periodontitis, alveolar bone loss, gingivitis, osteoporosis, osteopenia, oral bone resection, oral bone fracture, arthritis, osteoarthritis, osteotomy bone loss, osteolytic lesions, and childhood idiopathic bone loss. In another embodiment, the LXA$_4$ or analog thereof can be formulated in a pharmaceutically acceptable carrier, such as in mouth rinses, tooth pastes, dentifrice, buccal patch, dental fibre, dental tape, chewing gum, food additives, lozenges, tablet, chewable capsule, intraoral delivery devices, or encapsulated in resporbable carrier nanoparticles of biologic or synthetic origin. In still another embodiment, the effective amount of the LXA$_4$ or analog thereof is an amount that increases oral osteogenesis and/or reduces oral bone reabsorption. In yet another embodiment, the method further comprises administering at least one additional agent, such as anti-inflammatory agents and antimicrobial agents that treats the oral disorder that would benefit from increased oral osteogenesis. In another embodiment, the LXA$_4$ analog is 9,12 benzo-LXA$_4$. In still another embodiment, the administration is topical.

In another aspect, the present invention provides a method of treating periodontal disease in a subject in need thereof comprising: a) performing periodontal flap surgery upon at least one periodontal lesion of the subject; b) administering a therapeutically effective amount of LXA$_4$ or an analog thereof to the surgical wound at the time of surgery; to thereby treat the periodontal disease in the subject. In one embodiment, the periodontal disease can be, without limitation, periodontitis, gingivitis, chronic periodontitis, aggressive periodontitis, necrotizing periodontal disease, periodontium abcesses, and post-operative gingival infections. In another embodiment, the $LXA_4$ or analog thereof is formulated in a pharmaceutically acceptable carrier (nanoparticle of biologic or synthetic origin). In still another embodiment, the pharmaceutically acceptable carrier is selected from the group consisting of mouth rinses, tooth pastes, dentifrice, buccal patch, dental fibre, dental tape, chewing gum, food additives, lozenges, tablet, chewable capsule, and intraoral delivery devices. In yet another embodiment, the effective amount of the $LXA_4$ or analog thereof is an amount that increases oral osteogenesis and/or reduces oral bone reabsorption. In another embodiment, the method further comprises administering at least one additional agent, such as anti-inflammatory agents and antimicrobial agents that treats the periodontal disease. In still another embodiment, the $LXA_4$ analog is 9,12 benzo-$LXA_4$. In yet another embodiment, the administration is topical. In another embodiment, the method further comprises the step of administering a therapeutically effective amount of $LXA_4$ or an analog thereof, such as 9,12 benzo-$LXA_4$, to the at least one periodontal lesion at least one time after periodontal flap surgery completion. The additional method steps can further comprise administering at least one additional agent, such as anti-inflammatory agents and antimicrobial agents that treats the periodontal disease at least one time after periodontal flap surgery completion. These additional method steps can also use topical administration routes.

In addition, the detailed description provided herein discloses additional aspects of the present invention.

DETAILED DESCRIPTION OF THE INVENTION

The present invention is based, at least in part, on the discovery that $LXA_4$ and/or its analogs can increase oral osteogenesis and restore oral tissues. A single application of $LXA_4$ and/or its analogs to a debrided chronic periodontal lesion was unexpectedly sufficient to induce osteogenesis after periodontal flap surgery. Accordingly, methods of using $LXA_4$ and/or its analogs to treat or prevent oral disorders that would benefit from increased osteogenesis are provided herein. Methods for monitoring the progress of treating such disorders, as well as predicting the response to such treatment, are also provided herein.

A. Definitions

In order that the present invention may be more readily understood, certain terms are first defined. Additional definitions are set forth throughout the detailed description.

The articles "a" and "an" are used herein to refer to one or to more than one (i.e. to at least one) of the grammatical object of the article. By way of example, "an element" means one element or more than one element.

The term "analog" refers to any molecule having the basic structural components of a parent compound. Analogs of lipoxins encompass compounds containing a carboxyl component, a diol component, a tetraene component, and an alcohol component. These components can be any size and can be joined to one another in any manner. Additionally, these components can contain various substituents or have some of their carbon atoms replaced, for example, by rings or heteroatoms. Such analogs also retain at least one lipoxin activity but do not undergo the typical metabolic deactivation of the parent lipoxin compounds such that the in vivo half life of the compounds it significantly greater than that of the parent compounds. In some embodiments, lipoxin analogs have an "active region" that functions like the active region of a "natural lipoxin," but which has a "metabolic transformation region" that differs from the natural lipoxin. Such lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analog metabolites are also included. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers. In this context, the term "corresponding lipoxin" and "natural lipoxin" refer to a naturally-occurring lipoxin or lipoxin metabolite. An "active region" refers to the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Lipoxin $A_4$ analogs have an active region comprising C5-C15 of natural lipoxin $A_4$. The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A non-limiting example of a metabolic transformation region of a lipoxin is a portion of $LXA_4$ that includes the C-13,14 double bond or the C-15 hydroxyl group, or both. The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite. The term "resists metabolism" is meant to include failing to undergo one or more of the metabolic derivative transformations by at least one of the enzymes which metabolize lipoxins. Two non-limiting examples of LXA$_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form. The term "more slowly undergoes metabolism" means having slower reaction kinetics, or requiring more time for the completion of the series of metabolic transformations by one or more of the enzymes which metabolize lipoxin. A non-limiting example of an LXA$_4$ analog which more slowly undergoes metabolism is a structure which has a higher transition state energy for C-15 dehydrogenation than does LXA$_4$ because the analog is steric ally hindered at the C-16.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "body fluid" refers to fluids that are excreted or secreted from the body as well as fluids that are normally not (e.g. amniotic fluid, aqueous humor, bile, blood and blood plasma, cerebrospinal fluid, ceriman and earwax, Cowper's fluid or pre-ejaculatory fluid, chili, chime, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The term "bone" refers to the dense, semi-rigid, porous, calcified connective tissue forming the major portion of the skeleton of most vertebrates, comprising a dense organic matrix and an inorganic, mineral component. Bone is any of numerous anatomically distinct structures making up the skeleton of a vertebrate.

The term "bone healing" refers to restoring a bone and, optionally, the surrounding cartilage to, or to be closer to, their original or intended physical and mechanical properties when compared to such properties possessed by the bone prior to the start of such healing and/or prior to the injury, pathological destruction, pathological deterioration, surgical destruction, or surgical deterioration of the bone.

The term "bone mass" refers to bone mass per unit volume. A condition which presents with low bone mass is a condition where the level of bone mass is below the age specific normal level as defined in standards in "Assessment of Fracture Risk and its Application to Screening for Postmenopausal Osteoporosis," Report of a World Health Organization Study Group, World Health Organization Technical Series 843 (1994). A bone deficit is an imbalance in the ratio of bone formation to bone reabsorption, such that, if unmodified, the subject will exhibit less bone than desirable, or the subject's bones will be less intact and coherent than desired. Bone deficit can also result from fracture, from surgical intervention or from dental or periodontal disease. Bone healing includes, but is not limited to, repair of bone deficits, such as those occurring in, e.g., closed, open and non-union fractures.

The term "osteogenesis" refers to the net development and net formation of bone, including, without limitation the promotion of new bone growth and/or the alleviation of bone reabsorption. This can be achieved in a number of ways. For example, proliferation of bone cells results in growth of bone tissue (i.e., synthesis and deposit of new bone matrix) from undifferentiated stem cells and cells of osteoblast lineage. Bone tissue can also result from the differentiation or trans differentiation of progenitor or precursor cells into bone cells (i.e., osteoblasts). Progenitor or precursor cells can be pluripotent stem cells including, e.g., mesenchyme stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

B. Subjects

The terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human). In one embodiment, the subject for whom treatment or prevention of an oral disorder that would benefit from increased osteogenesis is a mammal (e.g., mouse, rat, primate, non-human mammal, domestic animal such as dog, cat, cow, horse), and is preferably a human. In some embodiments, the human is afflicted with or is suspected of having an oral disorder that would benefit from increased oral osteogenesis.

The terms "oral disorder" and "oral disorder that would benefit from increased oral osteogenesis" includes a disorder, disease or condition which is caused or characterized by an abnormally low or insufficient level of oral bone (e.g., bone in the oral cavity). Exemplary oral bone include alveolar bone and basal bone. Oral disorders that can be treated according to the invention, by increasing bone mass or bone growth include, but are not limited to, periodontal disease, alveolar bone loss, gingivitis, osteoporosis, osteopenia, oral bone resection, oral bone fracture, arthritis, osteoarthritis, osteotomy bone loss, childhood idiopathic bone loss, and the like. Destructive oral bone disorders that can be treated according to the invention include, but are not limited to, osteoporosis, osteopenia, osteoarthritis and osteolytic lesions such as those caused by neoplastic disease, radiotherapy, or chemotherapy. Also contemplated by the present invention is the regeneration of other oral tissues including soft tissues, epithelium, and connective tissues, such as collagen and blood vessels.

In some embodiments, periodontal diseases can be treated or prevented by using LXA$_4$ and/or its analogs to increase osteogenesis. A periodontium is a tissue which is present around teeth and plays a role in supporting teeth. The periodontium is composed of at least gingiva, alveolar bone, periodontal ligament (periodontal membrane), cementum, and dental pulp. Among periodontium inflammations, an inflammation confined to the gum is referred to as "gingivitis," while the case where inflammation sites extend beyond the gum to include damage and/or breakage of the periodontal membrane and/or alveolar bone is referred to as "periodontitis." A general term of these inflammations is "periodontal disease."

Periodontal diseases also encompass a larger set of inflammatory diseases affecting the periodontium. For example, such disease include dental plaque-induced gingival diseases; chronic (previously adult) periodontitis; aggressive periodontitis (formerly early-onset, prepubertal, juvenile or rapidly progressive periodontitis); necrotising periodontal diseases; abcesses of the periodontium; and post-operative bacterial infections (in particular those which are caused, transmitted and/or exacerbated by *P. gingivalis*).

Periodontitis involves progressive loss of the alveolar bone around the teeth, and, if left untreated, can lead to the loosening and subsequent loss of teeth. Periodontitis is caused by microorganisms that adhere to and grow on the tooth's surfaces, along with an overly aggressive immune response, against these microorganisms. Diagnosis of periodontal disease in general or periodontitis specifically is usually performed by measurement of a periodontal pocket, attachment level, X-ray image diagnosis, or the like. Periodontitis manifests as painful, red, swollen gums, with abundant plaque. Symptoms may include redness or bleeding of gums while brushing teeth, using dental floss, or biting into hard food (e.g., apples); recurrent swelling of the gum; halitosis and a persistent metallic taste in the mouth; gingival recession resulting in apparent lengthening of teeth; deep pockets between the teeth and the gums (pockets are sites where the attachment has been gradually destroyed by collagenases); and loose teeth. Thus, associated symptoms which may be treated according to the present invention include mouth ulcers, dental pain, discomfort, inflammation, bleeding, pus secretion, halitosis, tooth mobility, tooth loss, swelling or inflammation caused by any of the foregoing.

In 1999, a classification system was developed for periodontal diseases and conditions, which listed seven major categories of periodontal diseases, of which the last six are termed "destructive periodontal disease" because they are essentially irreversible. In addition, terminology expressing both the extent and severity of periodontal diseases were appended to the classes to further denote the specific diagnosis. The extent of disease refers to the proportion of the dentition affected by the disease in terms of percentage of sites. Sites are defined as the positions at which probing measurements are taken around each tooth and, generally, six probing sites around each tooth are recorded to make a determination of the extent of periodontal disease. Typically, if up to 30% of sites in the mouth are affected, the manifestation is classification as localized; if more than 30% of sites in the mouth are affected, the term generalized is used. The severity of disease refers to the amount of periodontal ligament fibers that have been lost, termed clinical attachment loss, and is defined by the American Academy of Periodontology as mild (1-2 mm of attachment loss), moderate (3-4 mm of attachment loss), or severe (≥5 mm of attachment loss).

C. $LXA_4$, $LXA_4$ Analogs, and Oral Formulations Thereof

Lipoxins are naturally-occurring lipid mediators derived from the fatty acid, arachidonic acid (Bazan (2006) in *Basic Neurochemistry: Molecular, Cellular and Medical Aspects, 7th edition*, G. Siegel et al. (eds.), Chapter 33:575-591; Mattson and Bazan (2006) in *Basic Neurochemistry: Molecular, Cellular and Medical Aspects, 7th edition*, G. Siegel et al. (eds.), Chapter 35:603-615. Lipoxins are potent mediators of the resolution phase of the inflammatory response and of dysfunctional immunity (Serhan et al. (1999) *Adv. Exp. Med. Biol.* 469:287-293; Fiorucci et al. (2004) *Proc. Natl. Acad. Sci. USA.* 101:15736-15741). There are several classes of lipoxins, such as $LXA_4$ and $LXB_4$, as well as analogs thereof that have been discovered/synthesized since the initial discovery of lipoxins in the 1980s. Specifically, lipoxin $A_4$ and its analogs, including lipoxin $A_4$ epimer 15 (or 15-epi-lipoxin $A_4$), are well known in the art (U.S. Pat. Nos. 6,831,186; 6,645,978; and 8,093,417; U.S. Pat. Publ. 2012/0149771; Fierro et al. (2003) *J. Immunol.* 170:2688-2694; Bannenberg et al. (2004) *Brit. J. Pharma.* 143:43-52; and Scalia et al. (1997) *Proc. Natl. Acad. Sci. USA* 94:9967-9972).

$LXA_4$ analogs are also well known in the art. Benzo-lipoxins have been found to be thermally and metabolically more stable than either of the endogenous lipoxins ($LXA_4$ and $LXB_4$). Replacement of the tetraene unit of $LXA_4$ with a benzo-fused ring also allows for efficient synthesis of these analogs. 9,12-$LXA_4$ is a member of this class of benzo-lipoxins and has been shown to have potent anti-inflammatory properties in a mouse model of acute inflammation, significantly reducing polymorphonuclear leukocyte (PMN) infiltration and levels of pro-inflammatory cytokines in vivo (Sun et al. (2009) *Prost. Leuokt. Essent. Fatty Acids* 81:357-366; Petasis et al. (2008) *Bioorg. Med. Chem. Lett.* 18:1382-1387).

In some embodiments, $LXA_4$ analogs can have one of the following structures:

These can be expanded to include additional $LXA_4$ analogs having one of the following structures having the designated stereochemistry:

In these structures, the R-groups are independently selected as follows:

R is hydrogen or a straight, branched, cyclic, saturated, or unsaturated alkyl;

$R^1$, $R^2$, $R^{12}$, $R^{13}$ are each independently selected from hydrogen; straight, branched, cyclic, saturated, or unsaturated alkyl having from 1 to 20 carbon atoms; substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl is substituted with one or more substituent selected from alkyl, cycloalkyl, alkoxy, halo, aryl, heteroaryl, carboxyl, and carboxamido;

and a group Z-Y, wherein Z is a straight, branched, cyclic, saturated, or unsaturated alkyl having from 1 to 20 carbon atoms; substituted lower alkyl wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido; and Y is selected from hydrogen; alkyl; cycloalkyl; carboxyl; carboxamido; aryl; heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido;

$R^3$ is selected from hydrogen; straight, branched, cyclic, saturated, or unsaturated alkyl having from 1 to 20 carbon atoms; substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and $R^4$-$R^{11}$ are selected from a group consisting of: hydrogen; halo; straight, branched, cyclic, saturated, or unsaturated alkyl having from 1 to 20 carbon atoms; substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl are substituted with one or more substituent selected from alkyl, cycloalkyl, alkoxy, halo, aryl, heteroaryl, carboxyl, and carboxamido;

R, $R^1$-$R^{13}$ may be also connected to form one or more rings containing 3 to 20 carbon atoms, 1 to 6 oxygen atoms or 1 to 6 nitrogen atoms.

A pair selected among the $R^1$-$R^{13}$ groups may also be replaced with a bond that generates a carbon-carbon double or triple bond or a ring.

Examples of exemplary, representative $LXA_4$ analogs are shown in Scheme 1. These examples are provided for purposes of illustration and in no way limit the scope of the present invention. Also contemplated as preferred compounds are the compounds shown in Scheme 1 wherein the carbon chains and rings shown in the structures additionally possess substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl.

-continued

Scheme 1

In some embodiments, LXA₄ and/or its analogs can be formulated with a physiologically compatible carrier medium. Such media can be of any simple type, e.g., a pharmaceutically acceptable carrier such as fructo-oligo-saccharide (FOS) medium, or other soluble fiber, sugar, nutrient or base material for the composition, with which the LXA₄ and/or its analogs can be formulated, e.g., in an orally administrable form. Other non-limiting, exemplary carrier media include mannitol, inulin (a polysaccharide), polydextrose, arabinogalactan, polyolslactulose, lactitol, etc. A wide variety of materials can be used as carrier material in the practice of the present disclosure, as will be apparent to those of ordinary skill in the art, based on the description herein.

The carrier medium, when present, can be blended with LXA₄ and/or its analogs in any suitable amounts, such as an amount of from 5% to 95% by weight of carrier medium, based on the total volume or weight of LXA₄ and/or its analogs and the carrier medium. In some embodiments, the amount of carrier medium can be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%. The amount of carrier medium in a specific embodiment may be determined based on considerations of the specific dose form, relative amounts of $LXA_4$ and/or its analogs, the total weight of the composition including the carrier medium and the bacterial species, and the physical and chemical properties of the carrier medium, and other factors, as known to those of ordinary skill in the $LXA_4$ formulation art.

$LXA_4$ and/or its analogs described herein can be formulated for oral administration. In some embodiments, the oral administration is targeted for application to the oral cavity, such as by applying the compositions and active ingredients contained therein to surfaces of the oral cavity, including but not limited to salivary glands, saliva, gingiva, dental plaque, teeth, tongue, cheek tissue, and the like. In some embodiments, the formulation is intended to adhere or otherwise contact the surgical wound area during periodontal flap surgery. The term "orally acceptable carrier" refers to one or more safe solid or liquid diluents or encapsulating substances compatible with $LXA_4$ and/or its analogs described herein and are suitable for topical oral administration. The term "compatible" means the substance is capable of being mixed with the $LXA_4$ and/or its analogs without interaction in a manner which would substantially reduce the agent's stability and/or efficacy. Non-exclusive examples of such orally acceptable carriers include distilled or deionized water, calcium carbonate, calcium citrate, bentonite, and montmorillonite.

The term "oral care composition" refers to any composition suitable for administration to the oral cavity of a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of an oral disorder that would benefit from increased oral osteogenesis; and combinations thereof. In various embodiments, an oral care composition is not intentionally swallowed for purposes of systemic administration of components of the composition, but is rather retained in the oral cavity for a time sufficient to contact substantially all of oral tissues for purposes of oral activity. The oral composition of the present invention may be in the form of a capsule, cachets, pills, lozenge, granules, toothpaste, tooth gel, subgingival gel, dentifrice, tooth powder, mouth rinse, denture product, mouth spray, oral tablet, oral device, chewing gum, oil-in-water emulsion, water-in-oil emulsion, elixir, syrup, or pastille using an inert base, such as gelatin and glycerin, or sucrose and acacia), or encapsulated in resporbable carrier nanoparticles of biologic or synthetic origin. Particles containing at least one component of a cellular-derived microparticle are described in L. Norling et al., *Journal of Immunology*, Cutting Edge: Humanized Nano-Proresolving Medicines Mimic Inflammation—Resolution and Enhance Wound Healing (published online Apr. 1, 2011) and in WO2012/135032, both of which are incorporated herein in their entirety by reference. The oral composition may also be incorporated onto strips or films for the application or attachment to oral surfaces. In certain embodiments, implants can be used, such as a chip for insertion into a periodontal pocket; a dental filling, bridge or cap; and a denture.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active agent, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, nanoparticle delivery vehicles can be used for oral administration.

The oral compositions for use in the present invention can be formulated with pharmaceutically acceptable carriers and/or diluents. The term "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Fndc5 expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In addition, the oral compositions useful for the present invention can comprise ingredients that are useful for more than simple oral formulation binding. Such optional ingredients generally are used individually at levels from about 0.0005% to about 10.0%, preferably from about 0.005% to about 1.0% by weight of the composition.

Examples of suitable optional ingredients include, but are not limited to, fluoride ion sources, alkali metal bicarbonate sources, humectants, anticalculus agents, abrasive polishing materials, thickening materials, surfactants, titanium dioxide, flavoring and sweetening agents, xylitol, coloring agents, teeth whitening agents, bentonite, montmorillonite, other active ingredients, and mixtures thereof.

Examples of suitable fluoride ion sources include, but are not limited to, sodium fluoride, potassium fluoride, sodium monofluorophosphate.

Examples of suitable alkali metal bicarbonate sources include, but are not limited to, sodium bicarbonate, and potassium bicarbonate.

Examples of suitable humectants include, but are not limited to, water soluble liquid polyols selected from the group comprising glycerine, propylene glycol, sorbitol, xylitol, butylene glycol, polyethylene glycol, and mixtures thereof.

Examples of suitable anticalculus agents include, but are not limited to, synthetic anionic polymers, including polyacrylates and copolymers of maleic anhydride or acid and methyl vinyl ether (e.g., Gantrez).

Examples of suitable abrasive polishing materials include, but are not limited to, silica, hydrated alumina, calcium carbonate, calcium citrate, dicalcium orthophosphate dihydrate, calcium pyrophosphate, tricalcium phosphate, calcium polymetaphosphate, and resinous abrasive materials.

Examples of suitable thickening materials include, but are not limited to, carboxyvinyl polymers, carrageenan, hydroxyethyl cellulose, water soluble salts of cellulose ethers such as sodium carboxymethylcellulose and sodium carboxymethyl hydroxyethyl cellulose, natural gums such as gum karaya, xanthan gum, gum arabic, and gum tragacanth, and mixtures thereof.

Examples of suitable surfactants include, but are not limited to, sodium and potassium salts of the following: lauroyl sarcosinate, myristoyl sarcosinate, palmitoyl sarcosinate, stearoyl sarcosinate and oleoyl sarcosinate.

Examples of suitable teeth whitening agents include, but are not limited to, talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Pigments that are generally recognized as safe, and are listed in C.T.F.A. Cosmetic Ingredient Handbook, 3rd Ed., Cosmetic and Fragrance Assn., Inc., Washington D.C. (1982).

Examples of suitable flavoring agents include, but are not limited to, oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof.

Examples of suitable sweetening agents include, but are not limited to, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof.

Examples of suitable antimicrobial agents include, but are not limited to, phenol and its homologs, mono and poly-alkyl and aromatic halophenols, resorcinol and its derivatives, bisphenolic compounds and halogenated salicylanilides, benzoic esters, and halogenated phenols, quaternary ammonium agents, copper bisglycinate, copper glycinate, zinc citrate, zinc lactate, chlorhexidine, triclosan, triclosan monophosphate, and flavor oils such as thymol.

Examples of suitable enzymes include, but are not limited to, proteases including papain, pepsin, trypsin, ficin, bromelin; cell wall lytic enzymes including lysozyme; plaque matrix inhibitors including dextranases, mutanases; and oxidases including glucose oxidase, lactate oxidase, galactose oxidase, uric acid oxidase, peroxidases including horse radish peroxidase, myeloperoxidase, lactoperoxidase, and chloroperoxidase.

Examples of antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In some embodiments, the oral compositions can further comprise one or more agents or regimens that can further treat the desired oral disorder that would benefit from increased oral osteogenesis.

For example, an anti-inflammatory substance can be added. Anti-Inflammatory agents are a well known class of pharmaceutical agents which reduce inflammation by acting on body mechanisms (Stedman's Medical Dictionary 26 ed., Williams and Wilkins, (1995); Physicians Desk Reference 51 ed., Medical Economics, (1997)). Anti-inflammatory agents useful in the methods of the invention include, without limitation, non-steroidal anti-inflammatory agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethacin, etodolac, ibuprofen, fenoprofen, ketoprofen, mefenamic acid, nabumetone, tolmetin sodium, and ketorolac tromethamine. Other anti-inflammatory agents useful in the methods of the invention include salicylates, such as, for example, salicylic acid, acetyl salicylic acid, choline salicylate, magnesium salicylate, sodium salicylate, olsalazine, and salsa late. Still other anti-inflammatory agents useful in the methods of the invention include cyclooxygenase (COX) inhibitors. COX catalyzes the conversion of arachidonate to prostaglandin H2 (PGH2); a COX inhibitor inhibits this reaction. COX is also known as prostaglandin H synthase, or PGH synthase. Two Cox genes, Cox-1 and Cox-2 have been isolated in several species. COX-2 is tightly regulated in most tissues and usually only induced in abnormal conditions, such as inflammation, rheumatic and osteo-arthritis, kidney disease and osteoporosis. COX-1 is believed to be constitutively expressed so as to maintain platelet and kidney function and integral homeostasis. Typical COX inhibitors useful in the methods of the invention include etodolac, celebrex, meloxicam, piroxicam, nimesulide, nabumetone, and rofecoxib.

In some embodiments, anti-inflammatory agents that can be incorporated into a polymer matrix for administration in the methods of the invention include, without limitation: 3-Amino-4-hydroxybutyric Acid, Aceclofenac, Acemetacin, Acetaminosalol, Alclofenac, Alminoprofen, α-Bisabolol, Paranyline, Amfenac, Bromfenac, Benoxaprofen, Benzpiperylon, Bermoprofen, Bromosaligenin, Bucloxic Acid, Bufexamac, Bumadizon, Butibufen, Carprofen, Cinmetacin, Clidanac, Clopirac, Diclofenac, Diclofenac Sodium, Diflunisal, Ditazol, Enfenamic Acid, ε-Acetamidocaproic Acid Bendazac, Etodolac, Etofenamate, Felbinac, Fenbufen, Fenclozic Acid, Fendosal, Fenoprofen, Fentiazac, Fepradinol, Flufenamic Acid, Flunoxaprofen, Flurbiprofen, Gentisic Acid, Glucametacin, Glycol Salicylate, Ibufenac, Ibuprofen, Ibuproxam, Indomethacin, Indoprofen, Isofezolac, Isoxepac, Isoxicam, Ketoprofen, Ketorolac, Lomoxicam, Lonazola, Lonazolac, Loxoprofen, Meclofenamic Acid, Mefenamic Acid, Meloxicam, Mesalamine, Metiazinic Acid, Mofebutazone, Mofezolac, Naproxen, Niflumic Acid, Olsalazine, Oxaceprol, Oxametacine, Oxaprozin, Oxicams, Oxyphenbutazone, Paranyline, Parsalmide, Perisoxal, Phenyl Salicylate, Pirazolac, Piroxicam, Pirprofen, Pranoprofen, Proprionic Acids, Protizinic Acid, Salacetamide, Salicilic Acid, Salicylamide O-Acetic Acid, Salicylsulfuric Acid, Salsalate, Sulfasalazine, Sulindac, Suprofen, Suxibuzone, Talniflumate, Tenoxicam, Terofenamate, Tiaprofenic Acid, Tiaramide, Tinoridine, Tolfenamic Acid, Tolmetin, Tropesin, Xenbucin, Ximoprofen, Zaltoprofen, Zileuton and Zomepirac.

For any anti-inflammatory agent referred to herein by a trade name it is to be understood that either the trade name product or the active ingredient possessing anti-inflammatory activity from the product can be used.

In other embodiments, the additional agents can induce osteogenesis and/or reduce bone reabsorption. For example, $LXA_4$ and/or its analogs can be administered in conjunction with bone morphogenetic proteins or anti-resorptive medications that affect the bone remodeling cycle. Suitable bone morphogenetic proteins include, for example, BMP-2, BMP-4, and BMP-7. Suitable anti-resorptive medications include, for example, flurbiprofen; bisphosphonates such as, for example, alendronate sodium and risedronate sodium; hormones, such as, for example, calcitonin and estrogens, and selective estrogen receptor modulators, such as, for example, raloxifene.

The described agents useful in combination with $LXA_4$ and/or its analogs can be administered simultaneously, concurrently or sequentially as the oral compositions or indeed formulated together with the oral compositions.

D. Methods

The methods of the present invention relate, at least in part, to the treatment or prevention of oral conditions that would benefit from increased oral osteogenesis including, for example, periodontitis or diseases associated with periodontitis. It has been described herein that $LXA_4$ and its analogs can be used to increase oral osteogenesis. Thus, $LXA_4$ and its analogs can be used in methods to increase oral osteogenesis and thereby treat or prevent oral conditions that would benefit from increased oral osteogenesis, such as periodontitis or diseases associated with periodontitis. Such methods involve administering an $LXA_4$ and/or an $LXA_4$ analog to oral surfaces in need of increased oral osteogenesis. Also contemplated by the present invention is the regeneration of other oral tissues including soft tissues, epithelium, and connective tissues, such as collagen and blood vessels.

As used herein, the term "agent" and "therapeutic agent" is defined broadly as anything that cells, tissues, or other surfaces of a subject having an oral disorder that would benefit from increased oral osteogenesis, such as the oral cavity, may be exposed to in a therapeutic protocol.

The term "administering" is intended to include routes of administration which allow the agent to perform its intended function. Oral administration routes are preferred and, in some embodiments, the oral administration is targeted for application to the oral cavity, such as by applying the compositions and active ingredients contained therein to surfaces of the oral cavity, including but not limited to salivary glands, saliva, gingiva, dental plaque, teeth, tongue, cheek tissue, and the like. The orally administered agents may be administered alone, or in conjunction with a pharmaceutically acceptable carrier and/or other active ingredients, such as anti-oral disorder that would benefit from increased oral osteogenesis agents, before, after, or simultaneously with the oral composition.

The term "effective amount" of an agent that treats or prevents an oral disorder that would benefit from increased oral osteogenesis is that amount necessary or sufficient to ameliorate the symptoms of the oral disorder. The effective amount can vary depending on such factors as the type of therapeutic agent(s) employed, the size of the subject, or the severity of the disorder.

By "treatment," "prevention," or "amelioration" of an oral disorder that would benefit from increased oral osteogenesis is meant delaying or preventing the onset of such a disease or disorder, reversing, alleviating, ameliorating, inhibiting, slowing down or stopping the progression, aggravation, deterioration or severity of a condition associated with such a disease or disorder. The term "treatment" is intended to encompass also prophylaxis, therapy and cure. The efficacy of a given treatment can be determined by the skilled clinician. However, a treatment is considered "effective treatment," as the term is used herein, if any one or all of the signs or symptoms of the oral disorder that would benefit from increased oral osteogenesis of interest, such as bone growth or density are altered in a beneficial manner, other clinically accepted symptoms or markers of disease are improved, or even ameliorated, e.g., by at least 10%, 20%, 30%, 40%, 50%, 60%, 70%, 80%, 90%, 95% or more following treatment with the agent. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting oral bone loss; or (2) relieving the disease, e.g., increasing oral bone growth; and (3) preventing or reducing the likelihood of the development of a complication from the oral disorder that would benefit from increased oral osteogenesis.

In practicing some embodiments of the present invention, a safe and effective amount of the compositions of the present invention may be topically applied to oral bone surfaces, mucosal tissue of the oral cavity, to the gingival tissue of the oral cavity, to the tongue, to the salivary glands, to the saliva, and/or to the surface of the teeth, soft tissues, epithelium, and connective tissues, such as collagen and blood vessels for the treatment or prevention of the above mentioned diseases or conditions of the oral cavity, preferably for at least about from 0.1 to about 10 minutes, more preferably from 0.5 to 1 minute in several conventional ways. For example, the gingival or mucosal tissue may be rinsed with oral solution compositions (e.g., mouth rinse, mouth spray) described herein. If the oral compositions described herein are in the form of a dentifrice (e.g., toothpaste, tooth gel or tooth powder), the gingival/mucosal tissue or teeth can be bathed in the liquid and/or lather generated by brushing the teeth. Other non-limiting examples include applying a non-abrasive gel or paste formulation of the oral compositions describe herein directly to the gingival/mucosal tissue, salivary glands, saliva, tongue, or to the teeth with or without an oral care appliance. Chewing gum oral formulations can be chewed and lozenges or tablets can be sucked. The administration methods can be reapplied or repeated from 1 to about 5, preferably from 1 to 3 times per day. Alternatively or in addition, oral delivery can be performed at a frequency of once to several times per day for 1, 2, 3, 4, 5, 6, or 7 days; or 1, 2, 3, or 4 weeks; or 1, 2, 3, 4, 5, 6, 7, 8, 9, 10, 11, or 12 months or longer (or any range in between). Typically, the effective amount of the composition is from about 0.5 to about 10 grams, preferably about 1 gram.

More generally, it will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular activate ingredients and its mode of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

In some embodiments, such as an adjunct to periodontal flap surgery, a single dose of $LXA_4$ and/or its analogs applied to the surgical wound under the flap has been determined herein to have a sustained, post-surgical effect on inducing oral osteogenesis. Thus, $LXA_4$ and/or its analogs can be used as an adjunct to periodontal flap surgery to increase oral osteogenesis in the periodontal pocket and treat associated oral disorders. Periodontal flap surgery is commonly performed to treat chronic periodontal lesions exhibiting significant bone loss in order to debride the lesioned area and remove deposits from the teeth. In general, when patients are not responsive to scaling and root planning procedures and/or antibiotic treatment, periodontal surgery, such as gingivectomy or periodontal flap surgery is often required. Such treatment methods are well known in the art. For example, in gingivectomy, the dentist reshapes the unhealthy gum tissue in order to reduce the size of the infected pocket. Reduction of the pocket size allows the patient to hygienically maintain the pocket by routine brushing and flossing, thereby eliminating a favorable environment for bacterial growth. Periodontal flap surgery is performed also when scaling and root planning procedures are unsuccessful, especially when there is loss of bone or tissue detachment. In this procedure, incisions are made in the gums and the surrounding alveolar bone is re-contoured to assist in healing of the infected area. Often, surgical treatments are insufficient in stimulating re-growth or replacement of the destroyed bone and cementum caused by severe periodontal disease such that the adjunct method using $LXA_4$ and/or its analogs described herein are especially useful.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any oral composition described herein to treat an oral disorder that would benefit from increased oral osteogenesis can be monitored by comparing two or more samples obtained from a subject undergoing treatment. In general, it is preferable to obtain a first sample from the subject prior to beginning therapy and one or more samples during treatment. In such a use, a baseline of expression of cells from subjects with the oral disorder prior to therapy is determined and then changes in the baseline state of expression of cells from subjects with the oral disorder that would benefit from increased oral osteogenesis is monitored during the course of therapy. Alternatively, two or more successive samples obtained during treatment can be used without the need of a pre-treatment baseline sample.

Whether one or more oral disorder(s) that would benefit from increased oral osteogenesis in a subject undergoing therapy are being ameliorated can be determined according to well-known assays in the art. For example, the following indicators can be monitored: 1) increase in bone growth and/or bone density; 2) decrease in bone loss and/or reversal of bone density loss; 3) decrease in tooth movement; 4) increase in osteoblast or bone-specific genes, such as alkaline phosphatase (ALP), collagen type I, osteocalcin, osteoponin, Cbfa1/Runx2, gsc, Dlx1, DlxS, Msx1, Cart1, Hoxa1, Hoxa2, Hoxa3, Hoxb1, rae28, Twist, AP-2, Mf1, Pax1, Pax3, Pax9, TBX3, TBX4, TBXS, and Brachyury (as determined by gene expression, enzymatic activity, immunohistochemistry, and the like; Olsen et al. (2000) Annu. Rev. Cell. Dev. Biol. 16:191); 5) decrease in periodontal pocket size; 6) increase in attachment level; 7) decreased tooth loss; 8) decreased periodontal inflammation; 9) decrease in periodontal disease progression stage; and combinations thereof.

In some embodiments, assays may involve subject samples. The term "sample," "tissue sample," "subject sample," "subject cell or tissue sample" or "specimen" each refer to a collection of similar cells obtained from a tissue of a subject. The source of the tissue sample may be solid tissue as from a fresh, frozen and/or preserved organ, tissue sample, biopsy, or aspirate relating to the oral cavity; or bodily fluids in contact with the oral cavity. The tissue sample may contain compounds that are not naturally intermixed with the tissue in nature such as preservatives, anticoagulants, buffers, fixatives, nutrients, antibiotics or the like.

In some embodiments, the amount and/or activity measurement(s) of a desired analyte, such as a bone protein, gene expression level, bone tissue and the like in a sample from a subject is compared to a predetermined control (standard) sample. The sample from the subject is typically from an oral source, such as saliva, dental plaque, gingiva, etc. The control sample can be from the same patient or from a different subject. The control sample is typically a normal, non-diseased sample. However, in some embodiments, such as for progression of disease or for evaluating the efficacy of treatment, the control sample can be from the subject at a different point in time or from a diseased tissue. The control sample can be a combination of samples from several different subjects. In some embodiments, the analyte amount and/or activity measurement(s) from a subject is compared to a pre-determined level. This pre-determined level is typically obtained from normal samples. As described herein, a "pre-determined" analyte amount and/or activity measurement(s) may be an analyte amount and/or activity measurement(s) used to, by way of example only, evaluate a subject that may be selected for treatment or evaluate a response to an oral osteogenesis-promoting therapy. A pre-determined analyte amount and/or activity measurement(s) may be determined in populations of patients with or without the disorder. The pre-determined analyte amount and/or activity measurement(s) can be a single number, equally applicable to every patient, or the pre-determined analyte amount and/or activity measurement(s) can vary according to specific subpopulations of patients. Age, weight, height, and other factors of a subject may affect the pre-determined analyte amount and/or activity measurement(s) of the individual. Furthermore, the pre-determined analyte amount and/or activity can be determined for each subject individually, such as based on the average or median analyte level in a relevant cohort (e.g., similarly aged subjects or subjects having similar oral disorder metrics). The pre-determined analyte amount and/or activity measurement(s) can be any suitable standard. For example, the pre-determined analyte amount and/or activity measurement(s) can be obtained from the same or a different human for whom a patient selection is being assessed. In one embodiment, the pre-determined analyte amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group or age.

In some embodiments of the present invention the change of analyte amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in analyte amount and/or activity measurement(s) compared to a predetermined level is more than about 1, more than about 5, more than about 10, more than about 20, more than about 30, more than about 40, or more than about 50.

The term "inhibit" includes the decrease, limitation, or blockage, of, for example a particular action, function, or interaction. In some embodiments, an oral disorder that would benefit from increased oral osteogenesis is "inhibited" if at least one symptom of the condition is alleviated, terminated, slowed, or prevented. In some embodiments, the term refers to a statistically significant decrease in a metric of interest indicative of an amelioration of an oral disorder that would benefit from increased oral osteogenesis. Such statistically significant decrease can be at least 10%, 20%, 30%, 40%, 50%, 60%, 70%, 80%, 90%, or more relative to a control. For example, a test compound administered and analyzed according to the methods described herein can comprise a bona fide increaser of oral osteogenesis by increasing oral osteogenesis by at least 10%, 20%, 30%, 40%, 50%, 60%, 70%, 80%, 90% or more relative to that of no agent administration or over a given amount of time.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the analyte amount and/or activity measurements of the subject obtained over time can be conveniently compared with each other, as well as with those of normal controls during the monitoring period, thereby providing the subject's own values, as an internal, or personal, control for long-term monitoring.

Exemplification

This invention is further illustrated by the following examples, which should not be construed as limiting.

Example 1: LXA$_4$ Analogs Increase Oral Osteogenesis in a Periodontal Disease Model A. Subjects The Institutional Animal Care Committee at the Forsyth Institute and PARF, Inc reviewed and approved the animal protocol prior any study activities. Two adult (18-24 months old) female minipigs (Hanford) were purchased and acclimatized for at least 7 days before any procedures. All surgical and follow up procedures and housing throughout the study duration (about 6 months including disease induction period) were performed at an animal and surgical facility at PARF, Inc.

B. Methods

Figure 1:
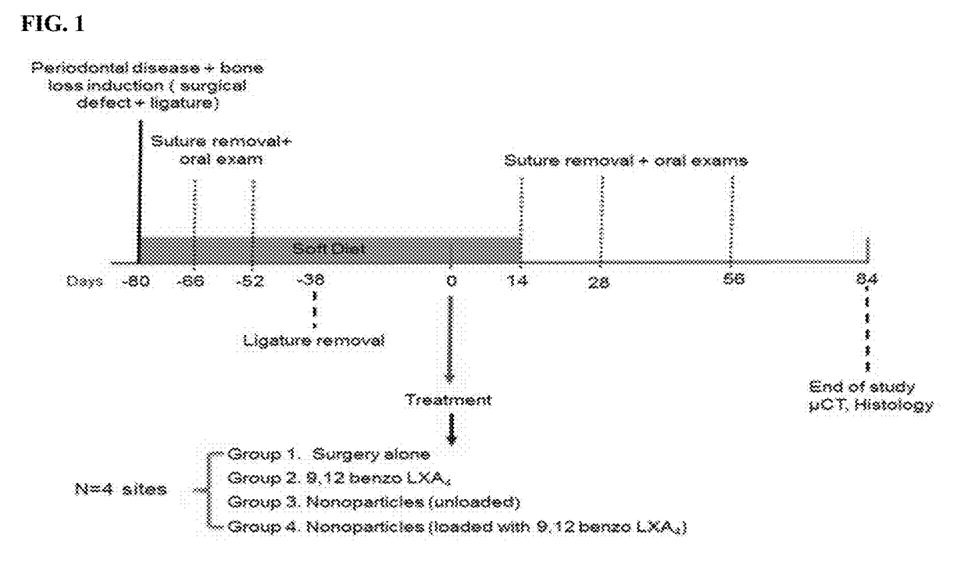
FIG. 1 shows a schematic diagram of an experimental protocol for treatment of periodontal disease and bone loss induction with 9,12 benzo $LXA_4$.
Figure 2A:
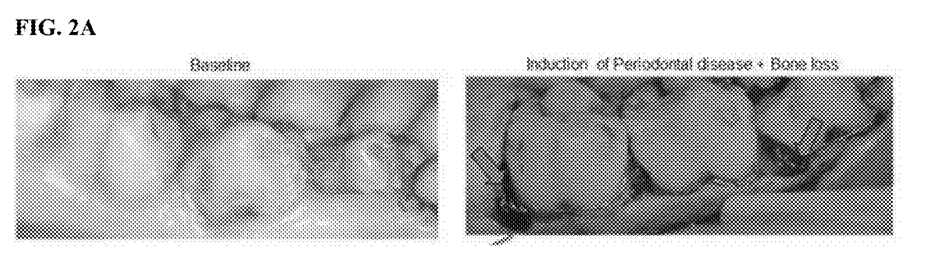
FIG. 2, contains three panels, showing representative visual images of teeth and surrounding tissues treated according to the indicated time points described in the experimental protocol described in FIG. 1.

FIG. 1 shows a summary of the experimental periodontal induction and treatment regimen. Anesthesia and surgical procedures were conducted as described in Hasturk H, Kantarci A, Ghattas M, Schmidt M, Giordano R, Ashman A, Diekwisch T, Van Dyke T E. The Use of Light/Chemically-Hardened Poly-Methyl-Methacrylate, Poly-Hydroxyl-Ethyl-Methacrylate and Calcium Hydroxide Graft Material in Combination with Polyanhydride around Implants in Minipigs: Part I: Immediate Stability and Function. J Periodontol. 2011 September; 82(9):1339-1352, which is incorporated by reference in its entirety herein. Briefly, minipigs were premedicated with Telazol (4-6 mg/kg IM) and xylazine (2.2 mg/kg IM) and were maintained by 3-4% isoflurane for induction and 0.5-2% isoflurane for maintenance. Each pig was anesthetized for approximately two hours during ligature placement and intraoral photographs. Endotracheal intubation was performed whenever the pig was fully anesthetized. Periodontal disease and bone loss were induced by creating intrabony defects using burs and ligatures in all four quadrants around the same teeth (second and fourth premolars) (FIG. 2A). After ligature placement, animals were fed with soft diet to stimulate plaque accumulation around ligatures for 6 weeks.

Figure 2B:
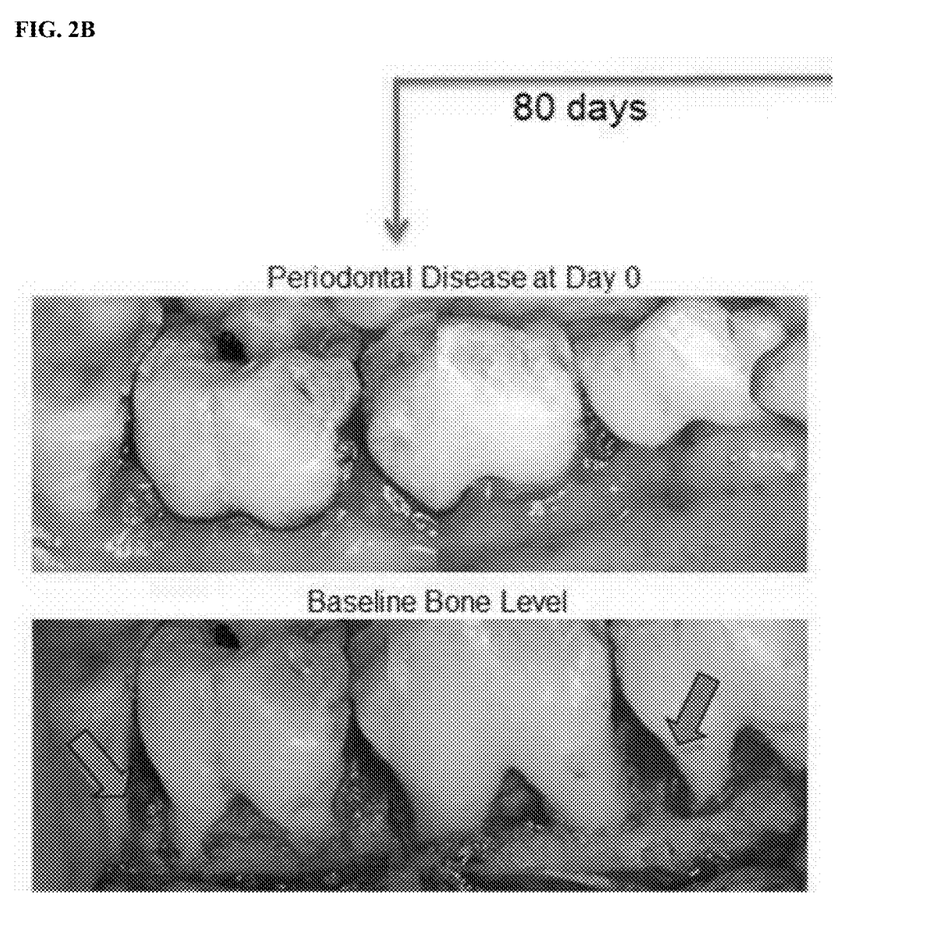

Oral examination, including digital photographs, were repeated at 2 and 4 weeks and ligatures were removed at 6 weeks. The sites were left untreated for about 38 days to stabilize the periodontal disease and bone loss obtained and to eliminate the self healing aspect of the bone defects. Accordingly, the defects were chronically created for the baseline treatments (FIG. 2B).

Figure 2C:
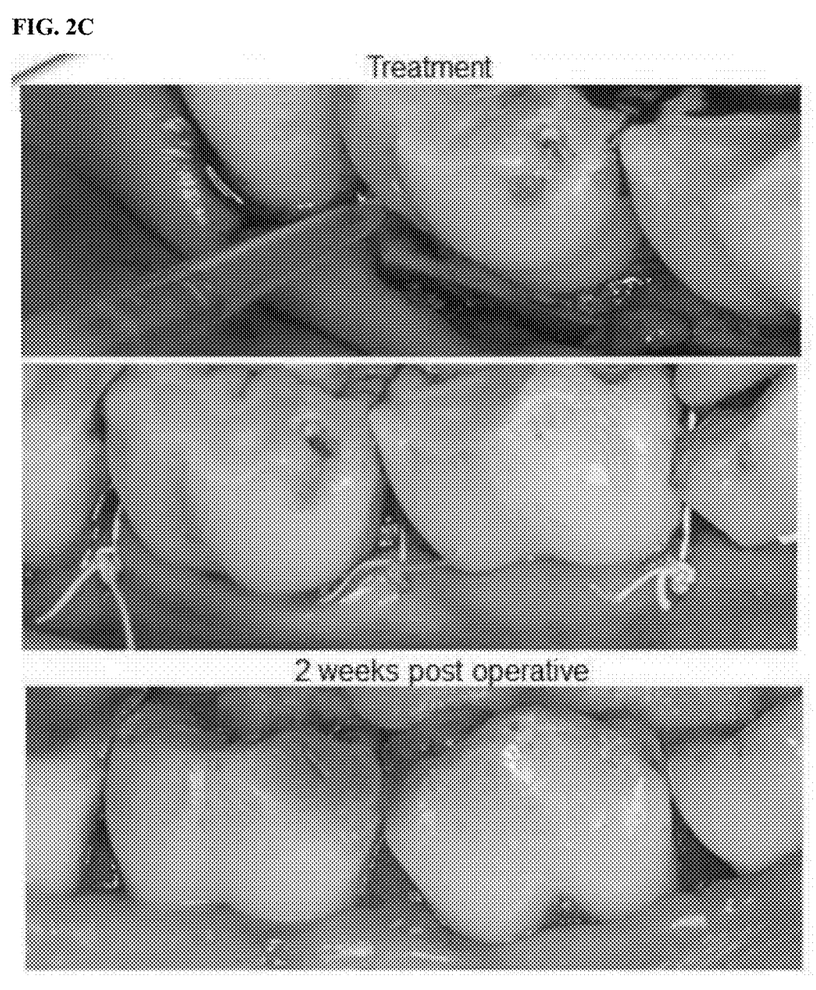

At Day 0 (baseline), the minipigs were anesthetized as described above. Blood samples were collected for serum collection. Subgingival plaque samples were collected from the treatment sites. Periodontal flaps were elevated mucoperiosteally. The defect areas were debrided, root surfaces were cleaned and scaled, and roots were planed. A notch was placed at the defect base. The sites were treated according to the randomization scheme for four treatment modalities: 1) surgery alone; 2) 9,12 benzo LXA$_4$; 3) nanoparticles-unloaded; and 4) nanoparticles loaded with 9,12 benzo LXA$_4$. LXA$_4$ was used in 0.1-1 µM range loaded in nanoparticles or alone. The delivery of nanoparticles or LXA$_4$ alone in a light gel form was made via plastic syringe (See in FIG. 2C). Vicryl sutures (size 4-0) were placed for primary closure and animals were placed on pain medication (buprenorphin) for 2-3 days. Sutures were removed at 2 weeks where a post operative oral exam was also conducted (FIGS. 2B-2C).

C. Results

Figure 3:
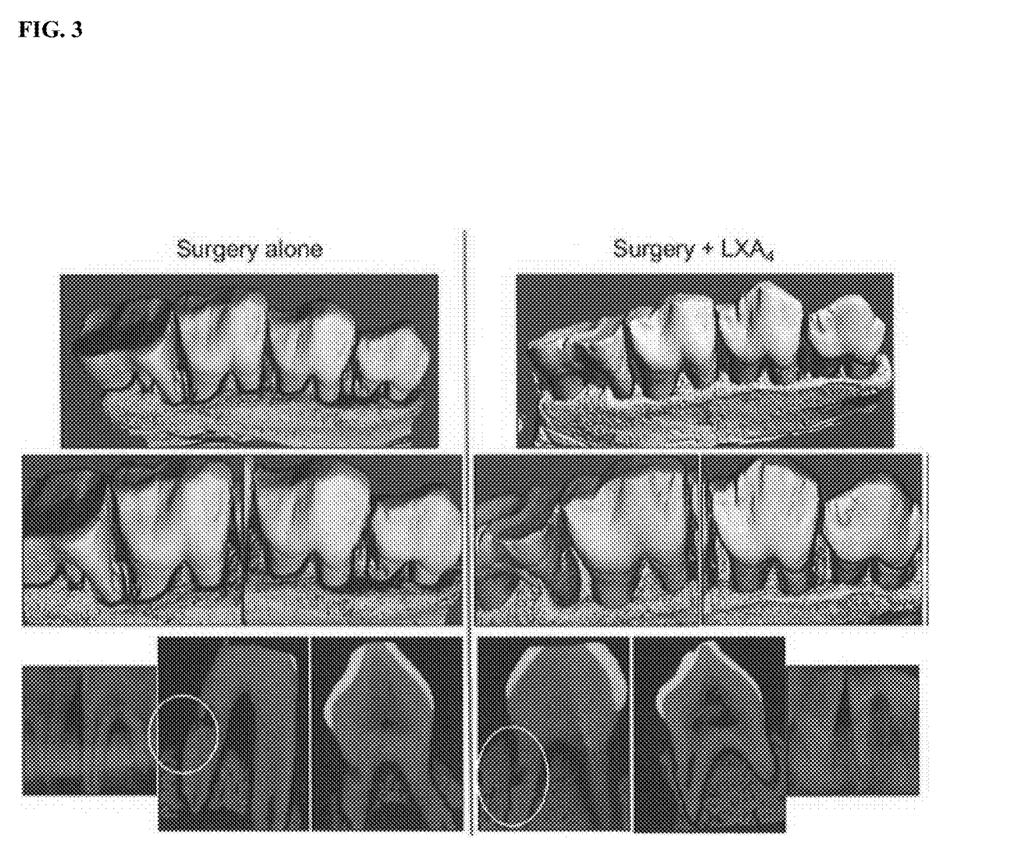
FIG. 3 shows micro-computer tomography and conventional radiographic images of representative teeth and surrounding tissues treated according to the experimental protocol described in FIG. 1.

Micro-computed tomography (µCT) imaging of teeth either treated with surgery alone or with surgery and application of 9,12, benzo LXA$_4$ indicate that induction of bone osteogenesis following LXA$_4$ treatment was observed (FIG. 3; see bone covering root notches). Conventional radiographic imaging of teeth either treated with surgery alone or with surgery and application of 9,12, benzo LXA$_4$ further indicate that the induced bone osteogenesis following LXA$_4$ treatment regenerated bone to essentially pre-disease levels (FIG. 3). Surprisingly and unexpectedly, the osteogenesis effects of 9,12, benzo LXA$_4$ on oral osteogenesis were observed after only a single application of 9,12, benzo LXA$_4$.

Incorporation by Reference

The contents of all references, patent applications, patents, and published patent applications, as well as the Figures and the Sequence Listing, cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method of increasing oral osteogenesis in a subject afflicted with a periodontal disease, the method comprising topically administering a therapeutically effective amount of a lipoxin A$_4$ (LXA$_4$) analog to the oral cavity of the subject, wherein the LXA$_4$ analog is 9,12 benzo-LXA$_4$, and wherein the 9,12 benzo-LXA$_4$ increases oral osteogenesis in the subject.

2. The method of claim 1, wherein the periodontal disease is selected from the group consisting of periodontitis, dental plaque-induced gingival diseases; chronic (previously adult) periodontitis; aggressive periodontitis (formerly early-onset, prepubertal, juvenile or rapidly progressive periodontitis); necrotizing periodontal diseases; abscesses of the periodontium; post-operative bacterial infections, alveolar bone loss, and gingivitis.

3. The method of claim 1, wherein the 9,12 benzo-LXA$_4$ is formulated in a pharmaceutically acceptable carrier.

4. The method of claim 3, wherein the pharmaceutically acceptable carrier is selected from the group consisting of gels, mouth rinses, toothpastes, dentifrice, buccal patch, dental fiber, dental tape, chewing gum, food additives, lozenges, tablet, and chewable capsule.

5. The method of claim 1, wherein the therapeutically effective amount of 9,12 benzo-LXA$_4$ is an amount that increases oral bone growth and/or reduces oral bone reabsorption.

6. The method of claim 1, further comprising administering to the subject at least one additional agent that treats periodontal disease.

7. The method of claim 6, wherein the additional agent is selected from the group consisting of anti-inflammatory agents and antimicrobial agents.

8. The method of claim 3, wherein the pharmaceutically acceptable carrier is an intraoral delivery device.

9. The method of claim 1, wherein the $LXA_4$ analog is encapsulated in a nanoparticle of biologic or synthetic origin.

10. The method of claim 1, wherein the therapeutically effective amount of 9,12 benzo-$LXA_4$ is an amount that increases oral osteogenesis by at least 10% relative to not administering the $LXA_4$ analog.

11. The method of claim 1, wherein the administering is to a subject undergoing periodontal flap surgery.

12. The method of claim 1, wherein the administering is to a subject has undergone periodontal flap surgery.

13. The method of claim 11, further comprising additionally administering a therapeutically effective amount of 9,12 benzo-$LXA_4$ to the subject one or more times after periodontal flap surgery completion.

* * * * *